(12) United States Patent
Schouten et al.

(10) Patent No.: US 11,060,197 B2
(45) Date of Patent: Jul. 13, 2021

(54) PROCESS FOR TREATING A DICARBOXYLIC ACID COMPOSITION

(71) Applicant: Avantium Knowledge Centre B.V., Amsterdam (NL)

(72) Inventors: Klaas Jan Pieter Schouten, Amsterdam (NL); Gerardus Johannes Maria Gruter, Amsterdam (NL); Jan Cornelis Van Der Waal, Amsterdam (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 32 days.

(21) Appl. No.: 16/463,756

(22) PCT Filed: Nov. 24, 2017

(86) PCT No.: PCT/NL2017/050775
§ 371 (c)(1),
(2) Date: May 23, 2019

(87) PCT Pub. No.: WO2018/097726
PCT Pub. Date: May 31, 2018

(65) Prior Publication Data
US 2019/0382905 A1    Dec. 19, 2019

(30) Foreign Application Priority Data
Nov. 24, 2016 (NL) ...................................... 2017869

(51) Int. Cl.
*C25B 3/23* (2021.01)
*C25B 3/25* (2021.01)
(Continued)

(52) U.S. Cl.
CPC ................ *C25B 3/23* (2021.01); *C07C 51/42* (2013.01); *C07D 307/68* (2013.01); *C25B 3/25* (2021.01);
(Continued)

(58) Field of Classification Search
CPC ................ C25B 3/04; C25B 3/23; C25B 3/25
(Continued)

(56) References Cited

U.S. PATENT DOCUMENTS 4,402,805 A * 9/1983 Donohue .................. C25B 3/04
                                                    205/443
4,521,556 A * 6/1985 Adams ................. C08K 5/0041
                                                    524/239
(Continued)

FOREIGN PATENT DOCUMENTS

GB            808118 A *  1/1959  ........... C07C 51/265
WO          199324440      12/1993

OTHER PUBLICATIONS

PCT Search Report (PCT/ISA/210) and Written Opinion of the International Searching Authority (PCT/ISA/237) by the ISA European Patent Office dated Mar. 6, 2018 for PCT application No. PCT/NL17/50775 filed Nov. 24, 2017 and published as WO 2018/097726 on May 31, 2018.

*Primary Examiner* — Edna Wong
(74) *Attorney, Agent, or Firm* — Suiter Swantz pc llo

(57) ABSTRACT

A process for treating a dicarboxylic acid composition, with the proviso that the dicarboxylic acid is not furan 2,5-dicarboxylic acid, which process comprises: —introducing a dicarboxylic acid composition, which dicarboxylic acid composition contains an impurity compound and which impurity compound is an organic compound comprising a carbonyl group, into a cathode compartment of an electro-
(Continued)

chemical cell; and electrochemically reducing the impurity compound in the cathode compartment.

19 Claims, 1 Drawing Sheet

(51) Int. Cl.
*C07D 307/68* (2006.01)
*C07C 51/42* (2006.01)
*C25B 11/03* (2021.01)
*C25B 11/057* (2021.01)
*C25B 9/19* (2021.01)

(52) U.S. Cl.
CPC ............ *C25B 11/03* (2013.01); *C25B 11/057* (2021.01); *C25B 9/19* (2021.01)

(58) Field of Classification Search
USPC ........................................ 205/413, 440, 443
See application file for complete search history.

(56) References Cited

U.S. PATENT DOCUMENTS

| | | | |
|---|---|---|---|
| 4,626,598 A | 12/1986 | Packer et al. | |
| 4,812,594 A | 3/1989 | Petty-Weeks | |
| 6,315,884 B1 * | 11/2001 | Putter | C25B 3/04 |
| | | | 205/440 |
| 2015/0008139 A1 * | 1/2015 | Saffron | C25B 3/00 |
| | | | 205/455 |

* cited by examiner

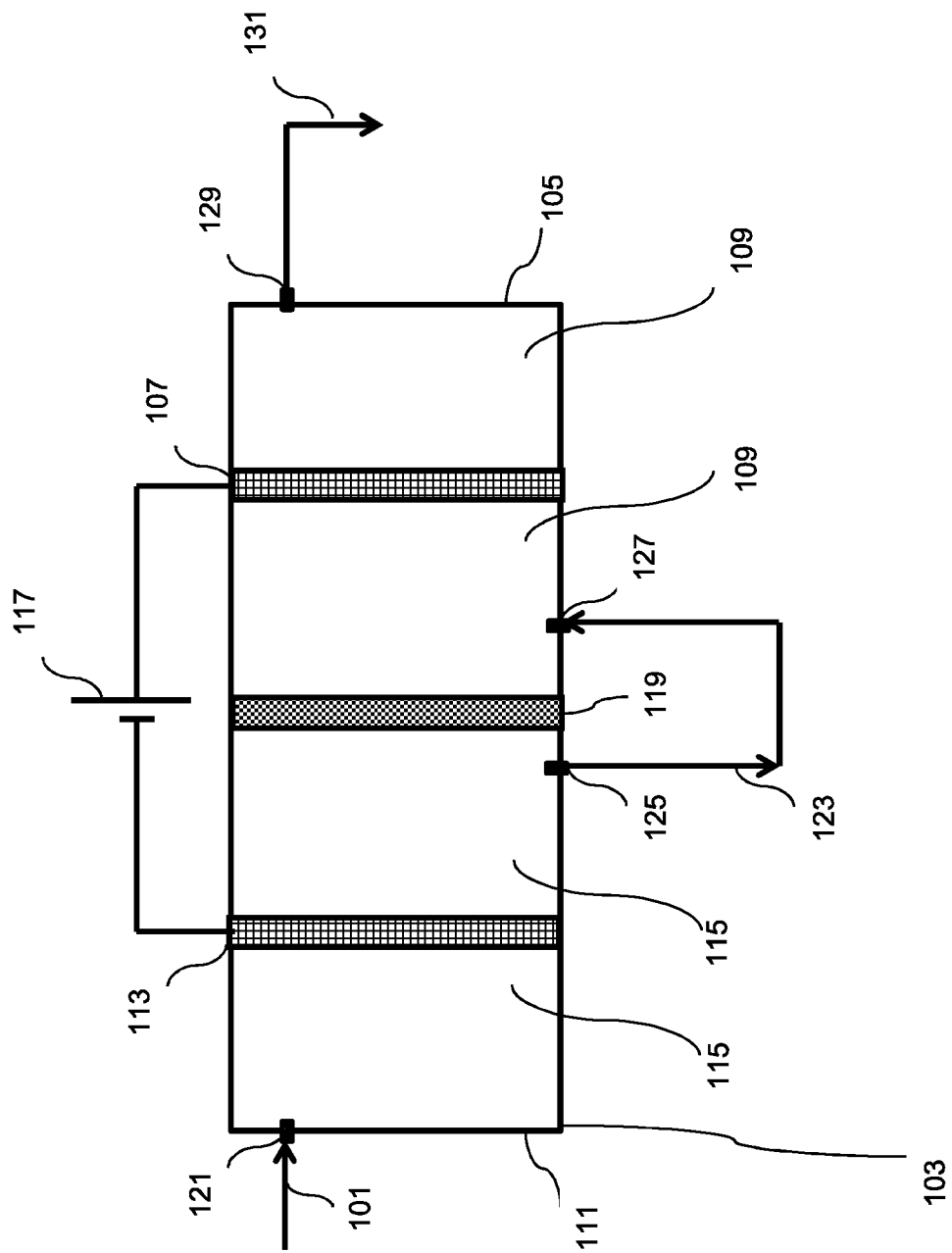

PROCESS FOR TREATING A DICARBOXYLIC ACID COMPOSITION

FIELD OF THE INVENTION

The invention relates to a process for treating a dicarboxylic acid composition.

BACKGROUND TO THE INVENTION

Dicarboxylic acids are widely used in the chemical industry as a starting material for the production of polymers.

For example, benzene-1,4-dicarboxylic acid (BDCA), also referred to as terephthalic acid, is used in the manufacture of polyester synthetic fibers such as poly ethylene terephthalate (PET).

The chemical preparation of polymer grade dicarboxylic acids, such as for example polymer grade benzene-1,4-dicarboxylic acid from relatively less pure or "crude" dicarboxylic acid is cumbersome.

As described in U.S. Pat. No. 4,892,972, even after purification, purified terephthalic acid contains color bodies and it is highly desirable to reduce the concentration for such color bodies that remain in purified terephthalic acid.

Norman Allen et al., in their article titled "Spectroscopic analysis of organic contaminants in terephthalic acid: color implications in poly(ethylene terephthalate) manufacture" published in Polymer Degradation and Stability vol. 62(2) pages 373-383 in November 1998 indicate that color measurements and doping experiments on PET show that the compounds in crude terephthalic acid which cause the yellow color of derived PET polymer are carboxylic acid derivatives of anthraquinone and fluorenone. They further indicate that fluorene derivatives are found to contribute to the PET polymer yellowness and further that 4-carboxybenzaldehyde (4-CBA) the major impurity in manufactured crude terephthalic acid, dominates the fluorescence spectrum. They suggest that associated dimers and aggregates of 4-CBA are primarily formed via the aldehyde and carboxylic acid groups.

U.S. Pat. No. 3,584,039 indicates that terephthalic acid impurities are of several types. According to U.S. Pat. No. 3,584,039 the compound 4-carboxybenzaldehyde, an intermediate product in the oxidation of para-xylene, is found in impure terephthalic acid and unidentified color-forming precursors and color bodies, possibly of the benzil, fluorenone or anthraquinone structure, are usually present.

In U.S. Pat. No. 4,892,972 a method is described for the purification of crude terephthalic acid, comprising a catalytic hydrogenation reaction at a temperature of from about 100° C. to 350° C., followed by cooling of the hydrogenated aqueous solution to effect separation of the resulting purified terephthalic acid from said solution by crystallization. The method described is evidently cumbersome and, as illustrated in example 6, a residual color remains.

WO 93/24440 describes a process for the production of purified terephthalic acid, comprising many steps, making it cumbersome and time-consuming to carry out. The described process is not illustrated with any examples and it is not clear how selective the process is.

It would be an advancement in the art to provide a process for the treatment of a dicarboxylic acid composition which is less cumbersome.

Non-pre published patent application WO2016/186504 describes a process wherein a feedstock comprising at least an aromatic aldehyde compound is introduced into an electrolytic cell comprising electrodes, wherein at least one of the electrodes comprises a non-noble metal and/or an oxide and/or a hydroxide thereof and/or carbon; and wherein the aromatic aldehyde compound is electrochemically oxidized to yield an aromatic dicarboxylic acid. According to examples 2 and 3 of WO2016/186504, the resulting products contained less color bodies. Non-pre published patent application WO2016/186505 describes a process for the purification of a carboxylic acid-containing composition, which composition further contains an aldehyde, which process comprises electrochemically oxidizing the aldehyde in an electrolytic cell to obtain an electrochemically oxidized product composition comprising a carboxylic acid derived from the aldehyde and optionally separating carboxylic acid from the electrochemically oxidized product composition.

Although good results are obtained with the processes of WO2016/186504 and WO2016/186505, there is still room for alternative processes and further improvement.

It would therefore be an advancement in the art to have a process with which similar, better, or economically more advantageous results can be achieved.

SUMMARY OF THE INVENTION

Such a process has been achieved with the process according to the invention. Accordingly the present invention provides a process for treating a dicarboxylic acid composition, with the proviso that the dicarboxylic acid is not furan 2,5-dicarboxylic acid, which process comprises:
  introducing a dicarboxylic acid composition, which dicarboxylic acid composition contains an impurity compound and which impurity compound is an organic compound comprising a carbonyl group, into a cathode compartment of an electrochemical cell; and
  electrochemically reducing the impurity compound in the cathode compartment.

By electrochemically reducing the impurity compound, the process is suitably producing one or more impurity reduction products.

The process according to the invention conveniently allows one to selectively reduce carbonyl groups, such as the aldehyde group in 4-formylbenzenecarboxylic acid (also known as 4-carboxybenzaldehyde). Conveniently such carbonyl groups can be selectively reduced, whilst carboxyl groups, such as the carboxyl groups of benzene-1,4-dicarboxylic acid (also known as terephthalic acid), are essentially maintained intact.

BRIEF DESCRIPTION OF THE DRAWINGS

FIG. 1 shows a schematic diagram of a first process according to the invention.

DETAILED DESCRIPTION OF THE INVENTION

The present invention relates to a process for treating a dicarboxylic acid composition, with the proviso that the dicarboxylic acid is not furan 2,5-dicarboxylic acid. That is, the dicarboxylic acid composition is a composition wherein a dicarboxylic acid other than 2,5-dicarboxylic acid is the predominant or main dicarboxylic acid. Consequently the dicarboxylic acid composition is not a furan 2,5-dicarboxylic acid composition.

By a dicarboxylic acid is herein understood an organic compound containing two carboxyl groups. Suitably the dicarboxylic acid is a dicarboxylic acid with chemical formula I:

HO—C(O)—R—C(O)—OH     (I)

wherein R represents an organic moiety. By an organic moiety is herein understood a moiety containing hydrogen and carbon atoms. In addition to such hydrogen and carbon atoms, the organic moiety can contain one or more heteroatoms such as nitrogen, sulphur or oxygen. The organic moiety can include one or more aliphatic groups, cycloaliphatic groups, aromatic groups and/or combinations thereof.

Preferably the dicarboxylic acid is an aromatic dicarboxylic acid. Therefore the organic moiety R in formula I preferably comprises at least one aromatic group. Suitably R represents an mono- or polycyclic aromatic moiety, for example an aromatic moiety corresponding to aromatic compounds such as benzene, naphthalene, anthracene or phenanthrene or corresponding to an oxygen-, nitrogen- or sulfur-containing heteroaromatic compound such as benzofuran, dibenzofuran, pyridine, quinolone, isoquinoline, or thiophene. Preferably, R is selected from the group consisting of phenylene, furylene and pyridylene moieties.

Most preferably the dicarboxylic acid is benzene-1,4-dicarboxylic acid (also referred to as terephthalic acid).

The dicarboxylic acid composition used in the process according to the invention can conveniently be a composition containing the dicarboxylic acid, the organic compound comprising a carbonyl group, and optionally one or more additional impurity compounds. Preferably the dicarboxylic acid composition is a dicarboxylic acid composition containing no or essentially no furan 2,5-dicarboxylic acid.

By an impurity compound is herein understood an organic compound other than the dicarboxylic acid. As explained in more detail below, such impurity compounds may or may not include colored compounds.

As described in in U.S. Pat. No. 3,584,039, examples of impurity compounds generated during the production of terephthalic acid include 4-carboxybenzaldehyde, unidentified color-forming precursors, and color bodies with a benzil, fluorenone or anthraquinone structure.

The process according to the invention is especially advantageous where the dicarboxylic acid composition contains or consists of a, preferably aromatic, dicarboxylic acid and a, preferably aromatic, organic compound comprising a carbonyl group.

The process is therefore preferably a process for treating an aromatic dicarboxylic acid composition, with the proviso that the aromatic dicarboxylic acid is not furan 2,5-dicarboxylic acid, which process comprises:
  introducing the aromatic dicarboxylic acid composition, which dicarboxylic acid composition contains an impurity compound and which impurity compound is a, preferably aromatic, organic compound comprising a carbonyl group, into a cathode compartment of an electrochemical cell; and
  electrochemically reducing the impurity compound in the cathode compartment.

By electrochemically reducing the impurity compound, the process is suitably producing one or more impurity reduction products.

As illustrated in the examples, the electrochemical process conveniently allows one to selectively reduce carbonyl groups, such as the aldehyde group in 4-formylbenzenecarboxylic acid. Conveniently such carbonyl groups can be selectively reduced, whilst carboxyl groups, such as the carboxyl groups of a benzene 1,4-dicarboxylic acid, are essentially maintained intact.

The organic compound comprising the carbonyl group can suitably be an aldehyde or a ketone. For example, the organic compound comprising the carbonyl group can be a dimer or polymer where the monomers are coupled via a carbonyl group. Preferably the organic compound comprising the carbonyl group is an aromatic compound comprising a carbonyl group, more preferably the organic compound comprising the carbonyl group is an aromatic compound comprising both a carbonyl group and a carboxyl group, such as 4-formylbenzenecarboxylic acid.

Preferably the organic compound comprising the carbonyl group is an aldehyde, and preferably the dicarboxylic acid composition contains or consists of a dicarboxylic acid and an aldehyde. More preferably the aldehyde is an aromatic compound comprising both an aldehyde group and a carboxyl group, such as 4-formylbenzenecarboxylic acid.

Most preferably the aldehyde is an aldehyde with chemical formula (II)

HO—C(O)—R—C(O)—H     (II)

wherein R represents an organic moiety as described above for the dicarboxylic acid.

The organic moiety R in the dicarboxylic acid and the organic moiety R in the aldehyde can be the same or different.

The process according to the invention can especially be advantageous where the dicarboxylic acid composition contains a dicarboxylic acid and its corresponding aldehyde and/or any dimer or co-polymer formed via the aldehyde and/or carboxylic acid groups of the dicarboxylic acid and its corresponding aldehyde. Preferably, the dicarboxylic acid composition contains a dicarboxylic acid with formula I:

HO—C(O)—R—C(O)—OH     (I)

and its corresponding aldehyde with formula II:

HO—C(O)—R—C(O)—H     (II)

wherein R represents the same organic moiety.

Preferably the dicarboxylic acid is benzene-1,4-dicarboxylic acid and the dicarboxylic acid composition contains such benzene-1,4-dicarboxylic acid and its corresponding aldehyde.

Preferably the dicarboxylic acid in the process according to the present invention is benzene-1,4-dicarboxylic acid and the impurity compound is 4-formylbenzenecarboxylic acid. More preferably the dicarboxylic acid composition contains or consists of benzene-1,4-dicarboxylic acid and 4-formylbenzenecarboxylic acid, and optionally a solvent.

Accordingly the present invention preferably provides a process for treating a benzene-1,4-dicarboxylic acid composition, which process comprises:
  introducing a benzene-1,4-dicarboxylic acid composition, which benzene-1,4-dicarboxylic acid composition contains an impurity compound and which impurity compound is 4-formylbenzenecarboxylic acid, into a cathode compartment of an electrochemical cell; and
  electrochemically reducing the impurity compound in the cathode compartment.

By electrochemically reducing the impurity compound, i.e. the 4-formylbenzenecarboxylic acid, the process is suitably producing one or more impurity reduction products, i.e. one or more of reduction products of 4-formylbenzenecarboxylic acid.

The dicarboxylic acid composition can suitably contain in the range from equal to or more than 1 parts per billion by weight (ppbw), more preferably equal to or more than 1 parts per million by weight (ppmw), to equal to or less than 50 wt %, more preferably equal to or less than 10 wt % of impurity compounds, based on the total weight of organic compounds in the dicarboxylic acid composition. More preferably the dicarboxylic acid composition can contain in the range from equal to or more than 10 ppmw to equal to or less than 1 wt % of impurity compounds, based on the total weight of organic compounds in the dicarboxylic acid composition. The remaining part of the organic compounds in the dicarboxylic acid composition is preferably made up of the dicarboxylic acid itself. Preferences for the dicarboxylic acid and the impurity compounds are as described above.

For example, where the dicarboxylic acid composition contains an aromatic dicarboxylic acid with formula I and a corresponding aromatic aldehyde with formula II as described above, the dicarboxylic acid composition can suitable contain in the range from equal to or more than 1 parts per billion by weight (ppbw), more preferably equal to or more than 1 parts per million by weight (ppmw), to equal to or less than 50 wt %, more preferably equal to or less than 10 wt % of such aldehyde with formula II, based on the total weight of the dicarboxylic acid and such corresponding aldhyde in the dicarboxylic acid composition. More suitably the dicarboxylic acid composition can contain in the range from equal to or more than 10 ppmw to equal to or less than 1 wt % of aldehyde with formula II, based on the total weight of the dicarboxylic acid and such corresponding aldehyde in the dicarboxylic acid composition.

Preferably the dicarboxylic acid composition is a benzene-1,4-dicarboxylic acid composition containing in the range from equal to or more than 1 parts per billion by weight (ppbw), more preferably equal to or more than 1 parts per million by weight (ppmw), to equal to or less than 50 wt %, more preferably equal to or less than 10 wt % of 4-formylbenzenecarboxylic acid, based on the total weight of organic compounds in the enzene-1,4-dicarboxylic acid composition. More preferably such benzene-1,4-dicarboxylic acid composition can contain in the range from equal to or more than 10 ppmw to equal to or less than 1 wt % of 4-formylbenzenecarboxylic acid, based on the total weight of organic compounds in the benzene-1,4-dicarboxylic acid composition. The remaining part of the organic compounds in the benzene-1,4-dicarboxylic acid composition can contain additional impurity compounds but is preferably made up of the benzene-1,4-dicarboxylic acid itself.

In addition to the dicarboxylic acid and impurity compounds, such as for example the 4-formylbenzenecarboxylic acid as described above, the dicarboxylic acid composition may or may not contain other non-organic compounds. For example in addition to the dicarboxylic acid and one or more impurity compounds, the dicarboxylic acid composition can contain an electrolyte solution as described below.

Aromatic dicarboxylic acids, such as benzene-1,4-dicarboxylic acid, are obtainable by or can suitably be obtained directly or indirectly by oxidation of the corresponding dialkyl aromatic compounds. For example benzene-1,4-dicarboxylic acid can be produced by means of a process comprising oxidation of the methyl groups of p-xylene in the presence of a soluble cobalt-manganese-bromine catalyst system, using acetic acid as solvent.

The process according to the invention may further be advantageous where the dicarboxylic acid composition used as a feed may have a significant color. As mentioned above the dicarboxylic acid composition may include one or more colored compounds, and as a result of their presence the dicarboxylic acid composition may have a distinguished color. The color level of such a dicarboxylic acid composition can be ascertained visually and/or any change of color can conveniently be measured by the so-called b*-value on the Hunter Color Scale as described in Hunter, "The measurement of Appearance", Chapter 8, pages 102-132, as published by John Wiley & Sons, NY, NY (1975) and in Wyszecki et al. "Color Science, Concepts and Methods, Quantitative Data and Formulae", $2^{nd}$ Ed., pages 166-168, John Wiley & Sons, NY, NY (1982). The b*-value of terephthalic acid can further be determined using, for example a Spectrophotometer as described for example in U.S. Pat. No. 4,626,598 and as incorporated herein by reference.

As illustrated in the above mentioned prior art, aromatic dicarboxylic acids, such as benzene-1,4-dicarboxylic acid, obtainable or obtained directly or indirectly by oxidation of the corresponding dialkyl aromatic compounds via the conventional methods as described above, can include an amount of colorants, also known as colored compounds. In conventional processes these colorants have to be removed by one or more re-crystallizations or by means of hydrogenation. Without wishing to be bound by any kind of theory it is believed that by means of reduction in the cathode compartment of an electrochemical cell also some colorants can possibly be removed, potentially facilitating the isolation of colorless product from the resulting product in the electrochemical cell.

Preferably, the dicarboxylic acid composition in the process according to the invention is partly or wholly obtained by means of electrochemically oxidizing a feedstock containing a dicarboxylic acid precursor.

Preferably the process therefore comprises:
introducing a feedstock containing a dicarboxylic acid precursor into an anode compartment of an electrochemical cell;
electrochemically oxidizing the dicarboxylic acid precursor in the anode compartment, thereby producing a dicarboxylic acid composition containing an impurity compound, which impurity compound is an organic compound comprising a carbonyl group;
introducing the dicarboxylic acid composition containing the impurity compound, into a cathode compartment of an electrochemical cell; and
electrochemically reducing the impurity compound in the cathode compartment.

As indicated above, the dicarboxylic acid is preferably benzene-1,4-dicarboxylic acid and the impurity compound is preferably 4-formyl-benzene-1-carboxylic acid.

By electrochemically reducing the impurity compound, such as for example the 4-formylbenzenecarboxylic acid, the process is suitably producing one or more impurity reduction products, such as for example one or more of reduction products of 4-formylbenzenecarboxylic acid.

More preferably the feedstock is a feedstock containing a dicarboxylic acid and a dicarboxylic acid precursor. Preferably such a feedstock containing a dicarboxylic acid and a dicarboxylic acid precursor is the product of an oxidation process as described above. Hence, preferably the feedstock is a feedstock containing an aromatic dicarboxylic acid and an aromatic dicarboxylic acid precursor, which is preferably obtained or obtainable by oxidation of a corresponding dialkyl aromatic compound. In such a process it may be advantageous to change the pH in between steps. That is, it may be advantageous to carry out the oxidation of the dicarboxylic acid precursor at a pH of equal to or more than 10, whilst carrying out the reduction of the one or more impurities at a pH of equal to or less than 4. Without wishing to be bound by any kind of theory it is believed that the product of an oxidation of a dialkyl aromatic compound as described in the prior art results in a crude aromatic dicarboxylic acid, which crude aromatic dicarboxylic acid contains the intended aromatic dicarboxylic acid and intermediate products, such as for example a formyl-substituted aromatic carboxylic acid or a hydroxyl-substituted aromatic carboxylic acid. Such intermediate products, for example a formyl-substituted aromatic carboxylic acid or a hydroxyl-substituted aromatic carboxylic acid, can be suitable dicarboxylic acid precursors in the feedstock to the above mentioned anode compartment and can suitably be electrochemically oxidized into the corresponding aromatic dicarboxylic acid.

In the process according to the invention, the dicarboxylic acid composition is introduced into a cathode compartment of an electrochemical cell. By a cathode compartment of an electrochemical cell is herein understood a compartment of an electrochemical cell containing a cathode, wherein suitably such cathode is a working electrode. By a working electrode is herein preferably understood an electrode in an electrochemical system at which a reaction of interest is occurring. In addition to the cathode the cathode compartment suitably contains a cathodic electrolyte solution. By a cathodic electrolyte solution is herein suitably understood an electrolyte solution present in the cathode compartment, which solution is in contact with the cathode.

By an anode compartment is herein understood a compartment of an electrochemical cell containing an anode, wherein suitably such anode is a working electrode. In addition to the anode the anode compartment suitably contains an anodic electrolyte solution. By an anodic electrolyte solution is herein suitably understood an electrolyte solution present in the anode compartment, which solution is in contact with the anode.

In the process according to the invention the cathode compartment and an optional anode compartment can suitably be part of the same divided electrochemical cell. Alternatively, the cathode compartment can suitably be part of a first, divided or undivided, electrochemical cell and the optional anode compartment can suitably be part of a second, divided or undivided, electrochemical cell.

If the electrochemical cell is an undivided electrochemical cell, the cathode, as a working electrode, is suitably accompanied by an anode, as a counter electrode. That is, the undivided electrochemical cell will contain both a cathode as well as an anode in the cathode compartment.

In a preferred embodiment the process according to the invention is a process comprising:
  introducing a dicarboxylic acid composition, which dicarboxylic acid composition contains an impurity compound, into an undivided electrochemical cell, which undivided electrochemical cell contains a cathode and an anode; and
  electrochemically reducing the impurity compound at the cathode.

As indicated above, the dicarboxylic acid is preferably benzene-1,4-dicarboxylic acid and the impurity compound is preferably 4-formyl-benzene-1-carboxylic acid.
By electrochemically reducing the impurity compound, such as for example the 4-formylbenzenecarboxylic acid, the process is suitably producing one or more impurity reduction products, such as for example one or more of reduction products of 4-formylbenzenecarboxylic acid.
In such a process the undivided electrochemical cell preferably further comprises an electrolyte solution having a pH of equal to or less than 4 or a pH of equal to or more than 10.

If the electrochemical cell is a divided electrochemical cell, the cathode, as a working electrode, is suitably located in a cathode compartment whilst the anode, whether as counter electrode or as working electrode, is suitably located in another compartment.

In a preferred embodiment the process according to the invention is a process comprising:
  introducing a dicarboxylic acid composition, which dicarboxylic acid composition contains an impurity compound, into an divided electrochemical cell, which divided electrochemical cell contains a cathode in a cathode compartment and an anode in a separate other compartment; and
  electrochemically reducing the impurity compound at the cathode.

As indicated above, the dicarboxylic acid is preferably benzene-1,4-dicarboxylic acid and the impurity compound is preferably 4-formyl-benzene-1-carboxylic acid.
By electrochemically reducing the impurity compound, such as for example the 4-formylbenzenecarboxylic acid, the process is suitably producing one or more impurity reduction products, such as for example one or more of reduction products of 4-formylbenzenecarboxylic acid.
In such a process the divided electrochemical cell preferably further comprises an electrolyte solution in the cathode compartment having a pH of equal to or less than 4 or equal to or more than 10, more preferably equal to or more than 13.

Preferably any electrochemical cell in the process according to the invention is a divided electrochemical cell, which divided electrochemical cell includes at least a cathode compartment and an anode compartment, wherein the cathode compartment contains a cathode and a cathodic electrolyte solution and the anode compartment contains an anode and an anodic electrolyte solution. The anode and cathode of such a divided electrochemical cell are suitably connected to a power supply, capable of applying a potential over the anode and cathode. The electrochemical cell may or may not further be provided with a reference electrode. If present, the reference electrode may be a standard hydrogen electrode. Such a standard hydrogen electrode may provide an indication for the potential to cause the reduction reaction. Preferably, however, the electrochemical cell is operated in the absence of a reference electrode.

The cathode compartment and the anode compartment in such a divided electrochemical cell are conveniently separated from each other, for example by a semi-porous membrane, made from e.g. sintered glass, porous porcelain, polytetrafluoro ethylene (PTFE or Teflon®) or polyolefin such as polyethylene or polypropylene. The electrolyte solution in the cathode compartment, i.e. the cathodic electrolyte solution, and the electrolyte solution in the anode compartment, i.e. the anodic electrolyte solution, can be the same or different.

The cathode and the anode may each be made of a variety of materials. The material of the cathode and the anode may for example each independently be chosen from the group consisting of gold, silver, nickel, palladium, platinum, chromium, ruthenium, rhodium, osmium, iridium, indium, bismuth, copper, tin, iron, lead and compounds or alloys thereof and/or hydroxydes and/or oxides thereof. Also carbon can also be used as the material of either or both the cathode and/or the anode, for example the cathode and/or the anode may contain or comprise graphite.

The cathode and/or anode, herein also referred to as electrodes, may suitably comprise noble metal with the oxide and/or hydroxide thereof. Such an electrode may be similar to the one used in the article by Grabowski et al. (Electrochimica Acta, 36 (1991) 1995). It has been found that the use of nickel or copper as material for the cathode and/or anode is advantageous.

The cathode and/or anode material can be present as a rod, plate, mesh, foam, cloth, or in the form of small particles deposited on a carrier, such as a carbon carrier.

Preferably the cathode contains or consists of copper, nickel, carbon, indium or bismuth, most preferably the cathode contains or consists of copper. Most preferably the cathode contains or consists of a copper or nickel mesh or a carbon cloth.

The electrolyte solution(s) can vary widely and can be any electrolyte solution known by the person skilled in the art to be suitable for an electrochemical reaction as set out in the currently claimed process. Preferably the electrolyte solution is an aqueous electrolyte solution. The electrolyte solution may, however, advantageously also contain or consist of acetic acid or methanol. Acetic acid and methanol are often used as solvent in a process comprising the oxidation of the corresponding dialkyl aromatic compounds, directly or indirectly resulting in the dicarboxylic acid composition as explained herein above. The process according to the present invention advantageously allows one to avoid any crystallization or recrystallization steps and advantageously allows one to use the aromatic dicarboxylic acid containing product of a process wherein a dialkyl aromatic compound is oxidized in the presence of an acetic acid or methanol solvent directly as feedstock in a process of the current invention.

The cathodic electrolyte solution in the cathode compartment containing the cathode preferably has a pH of equal to or below 4.0 or equal to or above 10.0. If the electrolyte solution is an aqueous electrolyte solution having a pH of equal to or more than 10.0, such electrolyte solution may also be referred to herein as an alkaline electrolyte solution. The alkalinity can facilitate the dissolution of the dicarboxylic acid. Suitably, such an alkaline electrolyte solution can comprise an alkaline compound selected from an alkali metal hydroxide, alkali metal carbonate, alkali metal bicarbonate, ammonia, ammonium carbonate, ammonium bicarbonate, a trialkylamine and combinations thereof. The use of weak acids and bases, such as carbonate and bicarbonate, has the advantage that they provide a buffering effect. The trialkylamine can suitably contain alkyl groups with 1 to 4 carbon atoms, preferably 1 or 2 carbon atoms. Suitable amines include trimethyl amine and triethyl amine. The aqueous electrolyte may comprise such an amount of an alkaline compound that the aqueous electrolyte, in spite of the presence of the dicarboxylic acid, is still alkaline. The pH of the aqueous electrolyte is then suitably in the range of 10.0 to 14.0.

If the electrolyte solution is an aqueous electrolyte solution having a pH of equal to or below 4.0, such electrolyte solution may also be referred to herein as an acidic electrolyte solution. The electrolyte solution may suitably be formed by the combination of water and dicarboxylic acid composition, and the ions are provided by the carboxyl function in the dicarboxylic acid and optionally one or more impurity compounds, when such impurity compound(s) also comprises a carboxyl group, such as 4-formylbenzenecarboxylic acid. Suitably the cathodic electrolyte solution may be an acetic aqueous electrolyte solution, suitably having a pH value of 0.5 to 4.0.

As already indicated above, the electrolyte solution does not need to consist of water and ions only. The electrolyte may conveniently also comprise one or more organic diluents. Suitable diluents include water-miscible organic compounds, such as alcohols, acids, aldehydes, ketones or sulfoxides. Examples of suitable diluents include methanol, ethanol, n-propanol, i-propanol, n-butanol, i-butanol and t-butanol, formaldehyde, acetone, acetic acid and dimethylsulfoxide. The electrolyte solution may further conveniently contain electrolytes derived from compounds such as sulfuric acid, perchloric acid and salts. A wide variety of electrolytes can be used, including for example sodium ($Na+$), chloride ($Cl-$), bromide ($Br-$), potassium ($K+$), magnesium ($Mg++$), zinc ($Zn++$), calcium ($Ca++$), phosphate ($HPO4-$) and bicarbonate ($HCO_3-$).

The electrolyte solution(s) preferably contain water at least in an amount of 5% wt, based on the total weight of the electrolyte solution, more preferably at least 50% wt, and most preferably at least 90% wt, based on the total weight of the electrolyte solution.

The temperatures applied during the electrochemical reduction and/or electrochemical oxidation may vary widely. Preferably the temperature applied during the electrochemical reduction and/or electrochemical oxidation ranges from equal to or more than 0° C., preferably equal to or more than 15° C., to equal to or less than 250° C., more preferably equal to or less than 200° C., still more preferably equal to or less than 150° C., even still more preferably equal to or less than 100° C., and most preferably equal to or less than 80° C. It is even possible to apply temperatures equal to or less than 60° C., as illustrated in the examples.

In the process according to the invention, an electrical potential is applied to the anode respectively the cathode. If the electrochemical cell in the process according to the invention is a divided electrochemical cell, and the above-mentioned cathode compartment and the above-mentioned anode compartment are present in the same divided electrochemical cell, the electrical potential is suitably applied between such anode and cathode of such divided electrochemical cell. If the above-mentioned cathode compartment is present in a first electrochemical cell and the above-mentioned anode compartment is present in a second, separate electrochemical cell, the electrochemical potential is suitably applied between the cathode, as working electrode, and a different anode, as counter electrode in the first electrochemical cell and between the anode, as working electrode, and a different cathode, as counter electrode, in the second electrochemical cell.

As illustrated in the examples, the process can suitably comprise reducing an organic compound comprising a carbonyl group, such as 4-formylbenzenecarboxylic acid, thereby producing one or more reduction products.

Without wishing to be bound by any kind of theory, it is believed that optionally a product composition can be obtained containing a, suitable colorless, dicarboxylic acid and one or more colorless reduction products.

The conditions in the electrochemical cell can vary widely, but one skilled in the art can easily determine the potential and current in the electrochemical cell of a sufficient magnitude to produce the chemical reactions desired. The potential difference between anode and cathode in the electrochemical cell or electrochemical cells, as applicable, is suitably below 10 V, more preferably below 1.23 V. By applying a voltage below 1.23 V the electrolysis of water is avoided. The desired voltage can be provided by installing a predetermined current or current density. The current may vary within wide limits as determined by the shape, size and other parameters of the electrochemical cell. Preferably the current density is varied between 0.1 mA/cm$^2$ and 10 A/cm$^2$, more preferably from 0.2 mA/cm$^2$ to 1 A/cm$^2$. The total current is adapted according to the surface of the smallest electrode. The reaction is typically prolonged at these conditions until the desired reactions take place.

The use of a divided electrochemical cell advantageously allows one to carry out one conversion in the cathode compartment and another conversion in the anode compartment.

The process according to the invention can conveniently be combined with the processes as described in WO2016/186504 and/or WO2016/186505. The processes as described in WO2016/186504 and/or WO2016/186505 can advantageously be carried out in the anode compartment of a divided electrochemical cell, or a second, separate electrochemical cell, whilst carrying out the process according to the current invention in the cathode compartment of the divided electrochemical cell, respectively a first electrochemical cell. As explained above, this conveniently allows one to prepare a, preferably purified, dicarboxylic acid composition in the anode compartment of the divided electrochemical cell, whereafter the dicarboxylic acid composition prepared in such anode compartment can advantageously to be introduced in the cathode compartment of another or the same divided electrochemical cell to further purify, and optionally decolorize, such dicarboxylic acid composition.

Preferably, the dicarboxylic acid composition that is introduced in the cathode compartment of a divided electrochemical cell, contains a dicarboxylic acid which has at least partly been obtained by oxidizing a feedstock containing one or more dicarboxylic acid precursors in the anode compartment of such same divided electrochemical cell. Preferably such feedstock containing one or more dicarboxylic acid precursors includes the corresponding alkanol, aldehyde or any mixture thereof of the dicarboxylic acid.

For example, the dicarboxylic acid that is introduced as part of the dicarboxylic acid composition in the cathode compartment of a divided electrochemical cell can be an aromatic dicarboxylic acid with chemical formula I:

HO—C(O)—R—C(O)—OH    (I)

wherein R represents an organic moiety comprising at least one aromatic group, which aromatic dicarboxylic acid has been obtained by:
providing a feedstock comprising at least an aromatic aldehyde compound of chemical formula II

HO—C(O)—R—C(O)—H    (II)

wherein R represents the same organic moiety comprising at least one aromatic group, into the anode compartment of the divided electrochemical cell; and
subsequently oxidizing the aromatic aldehyde compound electrochemically to thereby produce the aromatic dicarboxylic acid.

The present invention therefore also provides a process comprising treating a feedstock comprising a dicarboxylic acid and one or more dicarboxylic acid precursors in a divided electrochemical cell, which divided electrochemical cell comprises a cathode compartment containing a cathode and a cathodic electrolyte solution and an anode compartment containing an anode and an anodic electrolyte solution, which process comprises:
i) introducing the feedstock into the anode compartment of the divided electrochemical cell; and electrochemically oxidizing the dicarboxylic acid precursor at the anode to thereby produce a dicarboxylic acid composition, which dicarboxylic acid composition contains one or more impurity compounds; and ii) introducing the dicarboxylic acid composition into the cathode compartment of the divided electrochemical cell, and electrochemically reducing at least part of the one or more impurity compounds.

As explained above, the one or more impurity compounds may include colored compounds, and as a result of their presence the dicarboxylic acid composition may have a distinguished color.

Preferences for the impurity compounds and dicarboxylic acid composition are as described above. The feedstock used in the process comprising steps i) and ii) above preferably comprises an aromatic dicarboxylic acid obtained by oxidation of a dialkyl aromatic compound as described herein before. Preferences for the anode material and cathode material are also as described above. The pH of the anodic electrolyte solution, present in the anode compartment, may vary widely but preferably the anodic electrolyte solution has a pH of equal to or less than 4.0. Preferences for the anodic electrolyte solution in respect of the electrolyte are as described above for the cathodic electrolyte solution. The oxidation in step i) and the reduction in step ii) are suitably achieved by applying an electrical potential between the anode and the cathode of the electrochemical cell. Preferences for the potential and current are as described above.

The process according to the invention and the process comprising steps i) and ii) described above can suitably be carried out batch-wise, semi batch-wise or continuously. When carried out continuously the reduction in the cathode compartment of the divided electrochemical cell and the oxidation in the anode compartment of the divided electrochemical cell are conveniently carried out simultaneously.

The impurity reduction products, such as for example one or more reduction products of 4-formylbenzenecarboxylic acid, mentioned for the above processes may suitably comprise one or more organic compounds comprising a hydroxyl group. More suitably the impurity reduction products mentioned for the above processes may include one or more alcohols. For example where the impurity compound is 4-(formyl)benzenecarboxylic acid, the reduction compounds may comprise 4-(hydroxymethyl) benzenecarboxylic acid.

Where the dicarboxylic acid is benzene-1,4-dicarboxylic acid and the impurity compound is 4-formylbenzenecarboxylic acid, conveniently an electrochemically reduced product composition is obtained, comprising benzene-1,4-dicarboxylic acid and such 4-hydroxymethyl benzenecarboxylic acid. More preferably an electrochemically reduced product composition is containing benzene-1,4-dicarboxylic acid and in the range from equal to or more than 1 ppbw, more preferably equal to or more than 10 ppmw to equal to or less than 1 wt % of 4-hydroxymethyl benzenecarboxylic acid, based on the total weight of organic compounds in the electrochemically reduced product composition. The remainder of the organic compounds preferably consist predominantly (i.e. more than 60 wt %) of benzene-1,4-dicarboxylic acid.

Advantageously the process according to the invention comprises a further step of separating one or more impurity reduction products from the dicarboxylic acid. Such further step may comprise acidizing an electrolyte solution comprising the dicarboxylic acid and the one or more reduction products, thereby allowing the dicarboxylic acid and optionally one or more reduced products to precipitate to form a precipitated dicarboxylic acid composition. Such a composition could optionally comprise an essentially colorless dicarboxylic acid and essentially colorless derivatives of an aromatic compound comprising a carbonyl group.

FIG. 1 illustrates a non-limiting example of the processes according to the invention, wherein a feedstock comprising a dicarboxylic acid and one or more dicarboxylic acid precursors (101) is treated in a divided electrochemical cell (103), which divided electrochemical cell (103) comprises a cathode compartment (105) containing a copper mesh cathode (107) and a cathodic electrolyte solution (109), present on both sides of the copper mesh cathode (107), and an anode compartment (111) containing a copper mesh anode (113) and an anodic electrolyte solution (115), present on both sides of the copper mesh anode (113). The cathode (107) and anode (113) are connected to a power supply (117), which power supply provides a suitable potential over the anode and cathode to achieve the oxidation at the anode and the reduction at the cathode. The cathode compartment (105) and anode compartment (111) are separated from each other by means of a semi-porous membrane made from sintered glass (119). In the exemplary process of FIG. 1, the feedstock (101) is introduced into the anode compartment (111) via inlet (121). In the anode compartment (111) the feedstock (101) is contacted with the anode (113) to allow the dicarboxylic acid precursors to be oxidized into dicarboxylic acid such as to produce a dicarboxylic acid composition containing one or more impurity compounds. The produced dicarboxylic acid composition (123) is withdrawn from anode compartment (111) via outlet (125) and introduced via inlet (127) into the cathode compartment (105), where the dicarboxylic acid composition (123) is contacted with the cathode (107) and at least part of the one or more impurity compounds is electrochemically reduced to produce one or more impurity reduction products. The dicarboxylic acid and one or more impurity reduction products (131) are withdrawn from cathode compartment (105) via outlet (129) and forwarded to a crystallization unit to crystallize out a purified colorless dicarboxylic acid composition (not shown).

EXAMPLES

The invention is further illustrated by the following non-limiting examples

Example 1

A divided electrolytic cell consisting of an anode compartment and a cathode compartment separated from each other by means of a porous glass frit, was used. Both the anode and the cathode were nickel mesh electrodes. The electrolyte was 0.5M sodium hydroxide (NaOH). The reaction temperature was 20° C. and the current was 22.4 mA.

A feedstock comprising 50 millimole/liter (mM) of 4-formylbenzenecarboxylic acid and 50 mM of terephthalic acid was added to the cathode compartment. The electrochemical reduction was continued for about 5.6 hours. 9 samples of the cathodic electrolyte solution at the cathode were taken over the course of the experiment to determine the concentration of 4-formylbenzenecarboxylic acid, terephthalic acid and the concentration of reduction products A and B formed. The samples were analyzed by means of Gas Chromatography (GC), the detector was operated at a wavelength of 242 nm.

The results are shown in Table 1. The concentrations as reflected are in mM.

TABLE 1

Reduction of feedstock comprising a mixture of 4-formylbenzenecarboxylic acid and terephthalic acid

| Sample | Time (hour) | 4-formylbenzene carboxylic acid (mM) | Terephthalic acid (mM) | Reduction product A (mM) | Reduction product B (mM) |
|---|---|---|---|---|---|
| 1 | 0.1 | 44.40 | 53.80 | 0.96 | n.d.* |
| 2 | 0.7 | 38.30 | 53.78 | 1.99 | 2.47 |
| 3 | 1.4 | 27.44 | 54.54 | 3.54 | 9.25 |
| 4 | 2.4 | 14.80 | 54.20 | 5.32 | 16.73 |
| 5 | 3.1 | 7.24 | 53.85 | 6.43 | 21.18 |
| 6 | 4.2 | 2.26 | 53.40 | 7.24 | 23.81 |
| 7 | 5.1 | 0.66 | 52.79 | 7.53 | 24.41 |
| 8 | 5.6 | 0.33 | 52.54 | 7.60 | 24.38 |

*= not determined

The invention claimed is:

1. A process for treating a dicarboxylic acid composition containing a dicarboxylic acid and an impurity compound which is an organic compound comprising a carbonyl group, with the proviso that the dicarboxylic acid is not furan 2,5-dicarboxylic acid, which process comprises:
   introducing a feedstock containing a dicarboxylic acid precursor into an anode compartment of an electrochemical cell;
   electrochemically oxidizing the dicarboxylic acid precursor in the anode compartment, thereby producing the dicarboxylic acid composition;
   introducing the dicarboxylic acid composition into a cathode compartment of the electrochemical cell; and
   electrochemically reducing the impurity compound in the cathode compartment, thereby producing one or more impurity reduction products.

2. The process according to 1, wherein the feedstock containing the dicarboxylic acid precursor further includes the dicarboxylic acid.

3. The process according to claim 2, wherein the dicarboxylic acid is an aromatic dicarboxylic acid.

4. The process according to claim 2, wherein the dicarboxylic acid is an aromatic dicarboxylic acid obtained or obtainable, directly or indirectly, by oxidation of a corresponding dialkyl aromatic compound.

5. The process according to claim 2, wherein the dicarboxylic acid is benzene-1,4-dicarboxylic acid and the impurity compound is 4-formylbenzenecarboxylic acid.

6. The process according to claim 1, wherein the electrochemical cell is a divided electrochemical cell and the cathode compartment and the anode compartment are part of the same electrochemical cell.

7. The process according to claim 1, wherein the dicarboxylic acid composition further includes an aromatic dicarboxylic acid and the organic compound comprising the carbonyl group is an aromatic organic compound comprising the carbonyl group.

8. The process according to claim 1, wherein the cathode compartment further includes a cathodic electrolyte solution, which cathodic electrolyte solution has a pH of equal to or less than 4.0 or having a pH of equal to or more than 10.0.

9. The process according to claim 1, wherein the cathode compartment further contains a cathode including carbon or including a material selected from the group consisting of gold, silver, nickel, palladium, platinum, chromium, ruthenium, rhodium, osmium, iridium, indium, bismuth, copper, tin, iron, lead and compounds and alloys thereof and hydroxides and oxides thereof.

10. The process according to claim 1, wherein the cathode compartment further contains a cathode containing or consisting of a copper or nickel mesh or a carbon cloth.

11. The process according to claim 1, comprising a further step of separating the one or more impurity reduction products from the dicarboxylic acid.

12. The process according to claim 11, wherein the further step of separating the one or more impurity reduction products comprises acidizing an electrolyte solution comprising the dicarboxylic acid and the one or more impurity reduction products, thereby allowing the dicarboxylic acid and optionally the one or more reduction products to precipitate to form a precipitated dicarboxylic acid composition.

13. A process for treating a dicarboxylic acid composition containing a dicarboxylic acid and further an impurity compound which is an organic compound comprising a carbonyl group, with the proviso that the dicarboxylic acid is not furan 2,5-dicarboxylic acid, which process comprises:
  introducing a feedstock containing a dicarboxylic acid precursor into an anode compartment of an electrochemical cell;
  electrochemically oxidizing the dicarboxylic acid precursor in the anode compartment, thereby producing the dicarboxylic acid composition;
  introducing the dicarboxylic acid composition into a cathode compartment of another electrochemical cell; and
  electrochemically reducing the impurity compound in the cathode compartment, thereby producing one or more impurity reduction products.

14. The process according to 13, wherein the feedstock further includes the dicarboxylic acid and the dicarboxylic acid precursor.

15. The process according to claim 14, wherein the dicarboxylic acid is an aromatic dicarboxylic acid.

16. The process according to claim 14, wherein the dicarboxylic acid is an aromatic dicarboxylic acid obtained or obtainable, directly or indirectly, by oxidation of a corresponding dialkyl aromatic compound.

17. The process according to claim 14, wherein the dicarboxylic acid is benzene-1,4-dicarboxylic acid and the impurity compound is 4-formylbenzenecarboxylic acid.

18. The process according to claim 13, wherein the dicarboxylic acid composition further includes an aromatic dicarboxylic acid and the organic compound comprising the carbonyl group is an aromatic organic compound comprising the carbonyl group.

19. The process according to claim 13, wherein the cathode compartment further includes a cathodic electrolyte solution, which cathodic electrolyte solution has a pH of equal to or less than 4.0 or having a pH of equal to or more than 10.0.

\* \* \* \* \*